US 7,175,809 B2

(12) United States Patent
Gelfand et al.

(10) Patent No.: US 7,175,809 B2
(45) Date of Patent: Feb. 13, 2007

(54) FEEDBACK CONTROL OF ULTRAFILTRATION TO PREVENT HYPOTENSION

(75) Inventors: Mark Gelfand, New York, NY (US); John O'Mahony, Hackensack, NJ (US); Howard R. Levin, Teaneck, NJ (US)

(73) Assignee: CHF Solutions Inc., New York, NY (US)

( * ) Notice: Subject to any disclaimer, the term of this patent is extended or adjusted under 35 U.S.C. 154(b) by 35 days.

(21) Appl. No.: 10/801,059

(22) Filed: Mar. 16, 2004

(65) Prior Publication Data

US 2004/0176813 A1 Sep. 9, 2004

Related U.S. Application Data

(62) Division of application No. 09/755,298, filed on Dec. 29, 2000, now Pat. No. 6,706,007.

(51) Int. Cl.
*A61M 37/00* (2006.01)
*A61M 1/00* (2006.01)
*C02F 1/44* (2006.01)
*A61M 1/14* (2006.01)
*B01D 61/00* (2006.01)

(52) U.S. Cl. .................. 422/44; 604/6.09; 604/5.04; 604/6.11; 210/646; 210/741; 210/90

(58) Field of Classification Search ................ 210/654, 210/646, 739, 741, 85, 195.2, 327.1, 416.1, 210/433.1, 500.21, 645, 321.71, 90, 97; 604/4.01, 604/5.01, 5.04, 6.09, 6.11, 65–67; 422/44–48
See application file for complete search history.

(56) References Cited

U.S. PATENT DOCUMENTS 4,080,958 A 3/1978 Bregman et al.

(Continued)

FOREIGN PATENT DOCUMENTS

DE 26 44 062 9/1976

(Continued)

OTHER PUBLICATIONS

Piergiuseppe Agostoni et al., "Sustained Improvement in Functional Capacity After Removal of Body Fluid With Isolated Ultrafiltration in Chronic Cardiac Insufficiency: Failure of Furosemide to Provide the Same Result", Mar. 1994, The American Journal of Medicine, vol. 96, pp. 191-199.

(Continued)

*Primary Examiner*—Tatyana Zalukaeva
*Assistant Examiner*—Leslie Deak
(74) *Attorney, Agent, or Firm*—Nixon & Vanderhye P.C.

(57) ABSTRACT

A method and system for the extracorporeal treatment of blood to remove fluid from the fluid overloaded patient is disclosed that non-invasively measures an oxygen level in the venous blood. The oxygen blood level is used to detect when hypotension is about to occur in a patient. The oxygen level measurements are used as feedback signals. These feedback signals are applied to automatically control the rate of fluid extraction to achieve the desired clinical outcome and avoid precipitating a hypotensive crisis in the patient.

7 Claims, 5 Drawing Sheets

U.S. PATENT DOCUMENTS

| | | | |
|---|---|---|---|
| 4,086,924 A | | 5/1978 | Latham, Jr. |
| 4,657,529 A | | 4/1987 | Prince et al. |
| 4,710,164 A | | 12/1987 | Levin et al. |
| 4,739,492 A | * | 4/1988 | Cochran .................... 702/150 |
| 4,936,980 A | | 6/1990 | Yoshimichi et al. |
| 5,114,580 A | | 5/1992 | Ahmad et al. |
| 5,312,550 A | | 5/1994 | Hester |
| 5,351,686 A | | 10/1994 | Steuer et al. |
| 5,476,451 A | | 12/1995 | Ensminger et al. |
| 5,536,237 A | * | 7/1996 | Prince et al. ............. 604/6.11 |
| 5,685,989 A | | 11/1997 | Krivitski et al. |
| 5,707,086 A | | 1/1998 | Treu et al. |
| 5,725,776 A | * | 3/1998 | Kenley et al. ............. 210/646 |
| 5,906,589 A | | 5/1999 | Gordon et al. |
| 5,910,252 A | | 6/1999 | Truitt et al. |
| 6,090,048 A | | 7/2000 | Hertz et al. |
| 6,234,963 B1 | | 5/2001 | Blike et al. |
| 6,471,872 B2 | * | 10/2002 | Kitaevich et al. .......... 210/739 |
| 2002/0068015 A1 | | 6/2002 | Polaschegg et al. |

FOREIGN PATENT DOCUMENTS

| | | |
|---|---|---|
| WO | WO 97/15228 | 5/1997 |

OTHER PUBLICATIONS

Daniel Goldstein et al., "Venoarterial Shunting for the Treatment of Right Sided Circulatory Failure After Left Ventricular Assist Device Placement", ASAIO Journal 1997, pp. 171-176.

Michael Berkoben et al., "Hemodialysis Vascular Access", pp. 41-57.

Allan Lauer, "Continuous Arteriovenous Hemofiltration in the Critically Ill Patient", pp. 455-460.

A. L'Abbate et al., "Ultrafiltration: A Rational Treatment for Heart Failure", Cardiology 1989, pp. 384-390.

Yung-Chang Chen et al., "Direct Peripheral Venopuncture: Another New Choice of Temporary Vascular Access", pp. 369-377.

James Cimino et al., "Simple Venipuncture For Hemodialysis", The New England Journal of Medicine, Sep. 20, 1962, pp. 608-609.

Drukker et al., "Replacement of Renal Function by Dialysis", pp. 334-379.

Andrea Rimondini et al., "Hemofiltration as Short-Term Treatment for Refractory Congestive Heart Failure", Jul. 1987, The American Journal of Medicine, vol. 83, pp. 43-48.

Marc Silverstein et al., "Treatment of Severe Fluid Overload by Ultrafiltration", vol. 291, No. 15, Oct. 10, 1974, pp. 747-751.

Strife, C.F. et al, "Experience With a Low Volume Ultrafiltration Cell in Small Children," Clinical Nephrology 8:410-413 (1977).

Lauer, A. et al, "Continuous Arteriovenous Hemofiltration in the Critically Ill Patient, Clinical Use and Operational Characteristics," Annals of Internal Medicine 99:455-460 (1983).

Verbanck, J. et al, "Pure Ultrafiltration by Repeated Puncture of a Peripheral Arm-Vein as Treatment of Refratory Edema", The International Journal of Artificial Organs, vol. 3, No. 6 (1980), pp. 342-343.

Silverstein et al, "Treatment of Severe Fluid Overload by Ultrafiltration," The New England Journal of Medicine, vol. 291, No. 15, Oct. 10, 1974, pp. 747-751.

Blake, P. et al, "Refractory Congestive Heart Failure: Overview and Application of Extracorporeal Ultrafiltration," Critical Care Nephrology, *Advances in Renal Replacement Therapy*, vol. 3, No. 2 (Apr. 1966), pp. 166-173.

Civati G. et al, "Haemofiltration Without Substitution Fluid," Proc. EDTA-ERA, vol. 21 (1984), pp. 441-446.

Jenkins, R.D. et al, "The Use of Continuous Arteriovenous Hemofiltration With Hemodialysis in a Newborn," Draft #6, Personal Communication, 1985 (6 pages).

Jacobs, C. et al, "Continuous Arteriovenous Hemofiltration," Replacement of Renal Function By Dialysis, $4^{th}$ Ed., (1996) pp. 391-397.

Gupta, B.B. et al, "High Shear Rate Hemofiltration: Influence of Fiber Dimensions and Shear Rates," Artificial Organs, International Society for Artificial Organs, vol. 13(2) (1989), pp. 97-102.

Rimondini, A. et al, "Hemofiltration as Short-Term Treatment for Refractory Congestive Heart Failure," The American Journal of Medicine, vol. 83, Jul. 1987, pp. 43-48.

Donato, L. et al, "Treatment of End-Stage Congestive Heart Failure by Extracorporeal Ultrafiltration," The American Journal of Cardiology, vol. 59, (Feb. 1, 1987), pp. 379 and 380.

L'Abbate, A. et al, "Ultrafiltration: A Rational Treatment for Heart Failure," Cardiology 1989; 76:384-390.

Chen, Y. et al, "Direct Peripheral Venopuncture: Another New Choice of Temporary Vascular Access", Renal Failure, 22(3), 369-377 (2000).

* cited by examiner

FEEDBACK CONTROL OF ULTRAFILTRATION TO PREVENT HYPOTENSION

This is a divisional application that claims priority to and the benefit of the filing date of U.S. patent application Ser. No. 09/755,298 (now U.S. Pat. No. 6,706,007) filed Dec. 29, 2000, the entirety of which is incorporated by reference.

FIELD OF INVENTION

The present invention relates to an apparatus for the extracorporeal treatment of blood and more specifically to the automatic control of fluid removal from the blood of patients suffering from fluid overload and averting therapy induced hypotension.

BACKGROUND OF THE INVENTION

Renal Replacement Therapy (RRT) has evolved from the long, slow hemodialysis treatment regime of the 1960's to a diverse set of therapy options, the vast majority of which employ high permeability membrane devices and ultrafiltration control systems.

Biologic kidneys remove metabolic waste products, other toxins, and excess water. They also maintain electrolyte balance and produce several hormones for a human or other mammalian body. An artificial kidney, also called a hemodialyzer or dialyzer, and attendant equipment and supplies are designed to replace the blood-cleansing functions of the biologic kidney. At the center of artificial kidney design is a semipermeable filter membrane that allows passage of water, electrolytes, and solute toxins to be removed from the blood. The membrane retains in the blood, the blood cells, plasma proteins and other larger elements of the blood.

Over the last 15 years, the intended use of the RRT equipment the system has evolved into a subset of treatment alternatives that are tailored to individual patient needs. They include ultrafiltration, hemodialysis, hemofiltration, and hemodiafiltration, all of which are delivered in a renal care environment, as well as hemoconcentration, which is typically delivered in open heart surgery. Renal replacement therapies may be performed either intermittently or continuously, in the acute or chronic renal setting, depending on the individual patient's needs.

Ultrafiltration involves the removal of excess fluid from the patient's blood by employing a pressure gradient across a semipermeable membrane of a high permeability hemofilter or dialyzer. For example, removal of excess fluid occurs in hemoconcentration at the conclusion of cardiopulmonary bypass surgery. Hemodialysis involves the removal of toxins from the patient's blood by employing diffusive transport through the semipermeable membrane, and requires an electrolyte solution (dialysate) flowing on the opposite side of the membrane to create a concentration gradient. A goal of dialysis is the removal of waste, toxic substances, and/or excess water from the patients's blood. Dialysis patients require removal of excess water from their blood because they lack the ability to rid their bodies of fluid through the normal urinary function.

One of the potential risks to health associated with RRT is hypotension, which is an abnormal decrease in the patient's blood pressure. An abnormally high or uncontrolled ultrafiltration rate may result in hypovolemic shock, hypotension, or both. If too much water is removed from the patient's blood, such as might occur if the ultrafiltration rate is too high or uncontrolled, the patient could suffer hypotension and/or go into hypovolemic shock. Accordingly, RRT treatments must be controlled to prevent hypotension.

Alternatively, a patient may experience fluid overload in his blood, as a result of fluid infusion therapy or hyperalimentation therapy. Certain kinds of RRT machine failures may result in fluid gain rather than fluid loss. Specifically, inverse ultrafiltration may result in unintended weight gain of a patient and is potentially hazardous. Uncontrolled infusion of fluid by whatever mechanism into the patient could result in fluid overload, with the most serious acute complication being pulmonary edema. These risks are similar in all acute and chronic renal replacement therapies (ultrafiltration, hemodialysis, hemofiltration, hemodiafiltration, hemoconcentration). Monitoring patients to detect excessive fluid loss is needed to avoid hypotension.

Rapid reduction in plasma or blood volume due to excessive ultrafiltration of water from blood may cause a patient to exhibit one or more of the following symptoms: hypovolemia-hypotension, diaphoresis, cramps, nausea, or vomiting. During treatment, plasma volume in the patient's blood would theoretically remain constant if the plasma refilling rate equaled the UF (ultrafiltration) rate. However, refilling of the plasma is often not completed during a RRT session. The delay in refilling the plasma can lead to insufficient blood volume in a patient.

There appears to be a "critical" blood volume value below which patients begin to have problems associated with hypovolemia (abnormally decreased blood volume). Fluid replenishing rate is the rate at which the fluid (water and electrolytes) can be recruited from tissue into the blood stream across permeable walls of capillaries. This way blood volume is maintained relatively constant. Most of patients can recruit fluid at the rate of 500 to 1000 mL/hour. When patients are treated at a faster fluid removal rate, they begin to experience symptomatic hypotension.

Hypotension is the manifestation of hypovolemia or a severe fluid misbalance. Symptomatically, hypotension may be experienced by the patient first as light-headedness. To monitor patients for hypotension, non-invasive blood pressure monitors (NIBP) are commonly used during RRT. When detected early, hypotension resulting from the excessive loss of fluid is easily reversed by giving the patient intravenous fluids. Following administering fluids the RRT operator can adjust the ultrafiltration rate to make the RRT treatment less aggressive.

Ultrafiltration controllers were developed specifically to reduce the occurrence of hypotension in dialysis patients. Ultrafiltration controllers can be based on approximation from the known trans-membrane pressure (TMP), volume based or gravity based. Roller pumps and weight scales are used in the latter to meter fluids. Ultrafiltration controllers ensure the rate of fluid removal from a patient's blood is close to the fluid removal setting that was selected by the operator. However, these controllers do not always protect the patient from hypotension. For example, the operator may set the fluid removal rate too high. If the operator setting is higher than the patient's fluid replenishing rate, the operator should reduce the rate setting when the signs of hypotension manifest. If the excessive rate is not reduced, the patient may still suffer from hypotension, even while the controller operates properly.

Attempts were made during the last two decades to develop monitors that could be used for feedback control of dialysis machine parameters, such as dialysate concentration, temperature, and ultrafiltration rate and ultrafiltrate volume. Blood volume feedback signals have been proposed that are based on optical measurements of hematocrit, blood viscosity and blood conductivity. Real time control devices have been proposed that adjust the ultrafiltration rate to maintain the blood volume constant, and thereby balance the fluid removal and fluid recruitment rates. None of these proposed designs led to significant commercialization owing to the high cost of sensors, high noise to signal ratio or lack of economic incentive for manufacturers. In addition, many of these proposed systems required monitoring of patients by highly trained personnel.

Controllers that protect from hypotension are especially needed for patients suffering from fluid overload due to chronic Congestive Heart Failure (CHF). In CHF patients, fluid overload typically is not accompanied by renal failure. In these patients mechanical solute (toxins) removal is not required. Only fluid (plasma water) removal is needed. Ideal Renal Replacement Therapy (RRT) for these patients is Slow Continuous Ultrafiltration (SCUF) also known as "Ultrafiltration without Dialysis".

SCUF must be controlled to avoid inducing hypotension in the patient. Due to their poor heart condition, CHF patients are especially vulnerable to hypotension from excessively fast fluid removal. The clinical treatment objective for these patients can be formulated as: fluid removal at the maximum rate obtainable without the risk of hypotension. This maximum rate is equivalent to fluid removal at the maximum rate at which the vascular volume can be refilled from tissue. This maximum rate for CHF patients is typically in the 100 to 1,000 mL/hour range. The rate can vary with the patient's condition and is almost impossible to predict. The rate can also change over the course of treatment, especially if the objective of treatment is to remove 2 to 10 liters of fluid.

Hypotension in CHF patients often results from a decrease of the cardiac output of the patient. Cardiac output is the volume of blood that is ejected per minute from the heart as a result of heart contractions. The heart pumps approximately 4–8 L/min in a normal person. In a CHF patient cardiac output most often decreases because the heart is subject to a reduction of filling pressure. This dependency on the filling pressure is a well-known clinical consequence of the deterioration of the heart muscle during CHF. In a healthy person when the heart filling pressure is lowed, the heart will compensate and maintain cardiac output by working (e.g. pumping) harder. Filling pressure is the blood pressure in the right atrium of the heart. This pressure is approximately equal to the patient's venous pressure measured elsewhere in a great or central vein (such as vena cava) and corrected for gravity. In a fluid overloaded CHF patient Central Venous Pressure (CVP) is typically between 10 and 20 mmHg. If this pressure drops by 5 to 10 mmHg, the patient is likely to become hypotensive soon.

The danger of hypotension as a consequence of excessive fluid removal during dialysis and other extracorporeal blood treatments has been recognized. U.S. Pat. No. 5,346,472 describes a control system to prevent hypotension that automatically adjusts the sodium concentration added to the dialysate by infusing a hypertonic or isotonic saline solution in response to operator input or patient's request based on symptoms. European patent EU 0311709 to Levin and Zasuwa describes automatic ultrafiltration feedback based on arterial blood pressure and heart rate. U.S. Pat. No. 4,710,164 describes an automatic ultrafiltration feedback device based on arterial blood pressure and heart rate. U.S. Pat. No. 4,466,804 describes an extracorporeal circulation system with a blood oxygenator that manipulates the withdrawal of blood to maintain CVP constant. U.S. Pat. No. 5,938,938 describes an automatic dialysis machine that controls ultrafiltration rate based on weight loss or the calculated blood volume change. Late model AK200 dialysis machines from Gambro (Sweden) include an optional blood volume monitor called BVS or Blood Volume Sensor. This sensor is optical and in fact measures blood hematocrit or the concentration of red blood cells in blood. Since dialysis filter membranes are impermeable to blood cells, increased hematocrit signifies the reduction of the overall blood volume. The BVS sensor is not included in a feedback to the machine and is used to help the operator assess the rate of fluid removal.

U.S. Pat. No. 5,346,472 describes a mixed venous oxygen saturation responsive system for treating a malfunctioning heart. By sensing the change of the oxygen content in the venous blood the system adjusts the operation of a heart pacemaker. However, venous saturation of blood has never been used in adjusting an extracorporeal blood therapy for fluid removal such as ultrafiltration, hemofiltration or dialysis.

Other devices have been proposed that use arterial pressure as a feedback to the ultrafiltration controller to avoid hypotension. Automatic Non-Invasive Blood Pressure (NIBP) monitor feedback was used as a control system input. NIBP measures systolic and diastolic arterial blood pressure by periodically inflating a blood pressure cuff around the patient's arm or leg. Acoustic or oscillatory methods detect the pressure level at which blood vessels collapse. This level approximates systemic arterial blood pressure. Closed loop dialysis or fluid removal devices designed around this principle have several inherent deficiencies, including:

a) NIBP is inaccurate. Errors of up to 20 mmHg can be expected in the system. To avoid system oscillations and false alarms, the feedback would have to be slow and heavily filtered.

b) NIBP is not continuous, but is rather based on periodic pressure measurements. If the blood pressure cuff were inflated more frequently, less than every 15 minutes a patient would experience significant discomfort. Also, blood vessels change their elasticity from the frequent compressions of the blood cuff. This change in elasticity can add to the inaccuracy of cuff pressure measurements.

c) The arterial pressure in a CHF patient does not drop immediately following the reduction of cardiac output. It may take considerable time for a CHF patient to exhaust their cardiac reserve. By that time, the hypotension would have already occurred and its reversal would require medical intervention. Accordingly, hypotension may occur before NIBP detects it.

d) In a CHF patient, arterial blood pressure is maintained by the body to protect the brain. Neurohormonal signals are sent in response to baroreceptors that cause vasoconstriction of blood vessels to legs, intestine and kidneys. By sacrificing other body organs needs, arterial blood pressure to the brain can be kept constant at the expense of reduced blood flow to organs while the cardiac output is reduced dramatically.

Altogether, hypotension in a CHF patient can create a dangerous situation when the arterial blood pressure is apparently normal, while the overall condition of the patient is worsening. By the time the NIBP measurement has detected hypotension, serious medical intervention may be needed.

It is desired to have a feedback based control system that will continuously and automatically manipulate the ultrafiltration rate to achieve optimal ultrafiltration. In such a system, fluid is removed rapidly and without the risk of hypotension. It is also desired, in the application to CHF patients, to anticipate and correct the onset of the condition that before it is manifested by the reduction of arterial pressure.

SUMMARY OF THE INVENTION

A method and system has been developed for removing fluid from a fluid overloaded patient at a maximum safe rate that does not require human monitoring and interaction. The system senses oxygen saturation in a patient's venous blood as being indicative of conditions that cause hypotension. By monitoring oxygen saturation, the system detects the decrease of cardiac output that precedes the onset of hypotension and maintains a safe filtration rate by reducing or periodically turning off ultrafiltration when the oxygen saturation feedback signal indicates that hypotension may occur. Using the system that has an oxygen saturation feedback signal, hypotension is averted before it occurs.

A real time feedback system has been developed that:
a) Allows for an optimal rate of fluid removal in vulnerable CHF patients by automatically measuring and monitoring venous blood oxygen level, e.g., $SvO_2$, as indicators of the potential of hypotension.
b) Prevents episodes of hypotension so that fluid removal treatment can be conducted under minimal supervision.
c) Uses robust and inexpensive measurement system for monitoring the physiological blood parameters.

A method and system has been developed for removing fluid from a fluid overloaded patient at a maximum safe rate that does not require human monitoring and interaction to avoid hypotension. The system uses a physiologic blood variable, such as the oxygen level in blood, as being indicative of conditions that cause hypotension. The system maintains the physiological variable at a safe level by reducing or periodically turning off ultrafiltration. In this way hypotension is averted before it occurs.

In some instances, the absolute value of a physiologic blood variable or its significance is difficult to determine accurately. However, the change of the variable may be accurately determined, even if the absolute value of the variable is difficult to measure. During ultrafiltration treatment, the amount of change in a variable may be determined from a level of the variable established at the beginning of treatment. For example, a 20% drop of cardiac output during treatment is easier to detect than determining an absolute value for cardiac output or an absolute cardiac output value that is indicative of insufficient output. In particular, detecting a substantial drop of 20% in cardiac output may be more readily determined, than detecting when cardiac output falls below a 3 liter/minute threshold. Thus, an amount of change, rate of change and/or percentage change in a physiological blood parameter may be used to detect hypotension.

Mixed Venus Oxygen Saturation ($SvO_2$) provides a good estimate of the metabolic oxygen supply and demand and is related to cardiac output. When the cardiac output is decreased or when the cardiac output cannot compensate for increased oxygen utilization, the mixed venous oxygen content falls. $SvO_2$ represents the end result of both oxygen delivery and consumption at the tissue level for the entire body. Clinically, $SvO_2$ can be the earliest indicator of acute deterioration and is closely related to cardiac output. Venous blood is normally relatively unoxygenated, having not yet traveled through the lungs, with a saturation of 60–80%. The level of $SvO_2$ is a function of how much oxygen is being extracted from the blood by the organs. $SvO_2$ is an indicator of the supply and demand of oxygen to the tissues.

Arterial oxygen delivery is the product of cardiac output (QT) and arterial oxygen content ($Cao_2$); a reduction in either QT or $Cao_2$ threatens the adequacy of oxygen delivery. In either case (reduced QT or reduced CaO2), lactic acidosis and death will ensue if tissue oxygen uptake ($Vo_2$) is not maintained by the product of QT times the ($Cao_2-Cvo_2$) When cardiac output is decreased or when cardiac output cannot compensate for a decrease in $Cao_2$, the mixed venous oxygen content (and thus $SvO_2$ and $Pvo_2$) will fall. Thus, $SvO_2$ is a barometer of the adequacy of oxygen delivery ($QT \times Cao_2$) for the body's oxygen needs.

During RRT treatment of a fluid overloaded patient, $SvO_2$ should remain within normal ranges, and change very little. Hemoglobin content and oxygen consumption should vary only slightly during the 4–8 hour of treatment for fluid overload. A sudden decrease of $SvO_2$ is most likely an indication of sudden drop of cardiac output and a precursor of hypotension. Accordingly, detecting a substantial change in $SvO_2$ levels can be used as an indicator of hypotension and used to reduce a blood treatment rate, such as an ultrafiltration rate.

Venous blood oxygen saturation is an accepted indicator of the remaining oxygen content in the venous blood. Hemoglobin (Hb), an intracellular protein, is the primary vehicle for transporting oxygen in the blood. Hemoglobin is contained in erythrocytes, more commonly referred to as red blood cells. Oxygen is also carried (dissolved) in plasma, but to a much lesser degree. Under conditions of increased oxygen utilization by the tissues, oxygen that is bound to the hemoglobin is released into body tissue. When the patient inhales, oxygen from the air is absorbed in the blood, as the blood passes through lungs. Each hemoglobin molecule in the blood has a limited capacity to bond to oxygen molecules. Oxygen saturation is the degree to which the capacity to bind to oxygen is actually filled by oxygen bound to the hemoglobin. Oxygen saturation, when expressed as a percentage, is the ratio of the amount of oxygen molecules bound to the hemoglobin, to the oxygen carrying capacity of the hemoglobin. The oxygen carrying capacity is determined by the amount of hemoglobin present in the blood.

Moreover, $SvO_2$ changes can be measured non-invasively using pulse oximetry. Non-invasive photoelectric pulse oximetry has been previously described in U.S. Pat. Nos. 4,407,290, 4,266,554, 4,086,915, 3,998,550 and 3,704,706. Pulse oximeters are commercially available from Nellcor Incorporated, Pleasanton, Calif., U.S.A., and other companies for integration in medical devices.

Pulse oximeters typically measure and display various blood flow characteristics including but not limited to blood oxygen saturation of hemoglobin in arterial blood. The oximeters pass light through human or animal body tissue where blood perfuses the tissue such as a finger, an ear, the nasal septum or the scalp, and photoelectrically sense the absorption of light in the tissue. The amount of light absorbed is then used to calculate the amount of blood constituent being measured. The light passed through the tissue is selected to be of one or more wavelengths that is absorbed by the blood in an amount representative of the amount of the blood constituent present in the blood. The amount of transmitted light passed through the tissue will vary in accordance with the changing amount of blood constituent in the tissue and the related light absorption.

For example, the Nellcor N-100 oximeter is a microprocessor controlled device that measures oxygen saturation of hemoglobin using light from two light emitting diodes ("LED's"), one having a discrete frequency of about 660 nanometers in the red light range and the other having a discrete frequency of about 925 nanometers in the infrared range.

Since in a RRT machine blood circulates outside of the body through a transparent plastic tube, the photometric method of oximetry can be easily adapted for the application. Light emitting LED's and the light receiving device can be placed on the opposite sides of the tube. Device can be calibrated to subtract the affects of the tubing on the measurement.

During the fluid removal treatment in a CHF patient, central venous blood is not always available. In some cases in acute RRT treatment so called central venous catheters are used for blood withdrawal and return. These catheters are advanced from a femoral, jugular or subclavian veins. The tip of the catheter is advanced deep into the body until central access to venous blood is established. Such catheters can draw true mixed venous blood similar in composition to the blood in the right atrium of the heart. Such catheters are associated with high risks that are not always acceptable.

It is desired to have a device for treatment of fluid overloaded CHF patients that will only draw blood from a peripheral vein that is always available. Suitable peripheral veins are the veins in the arm of the patient. The tip of the catheter can be located in a relatively small vein in the middle of the arm or could be advanced close to the shoulder. In the latter case, if the tip has past venous valves, the blood in the extracorporeal circuit will be similar in composition to the blood in a central vein. Although oxygen saturation in the blood from a peripheral vein reflects both global and local organ oxygen extraction, and can be used to detect low cardiac output based on measurements of $SvO_2$. Accordingly, $SvO_2$ changes can be monitored during blood treatments that use central, mid line (closer to the shoulder) and peripheral blood access.

BRIEF DESCRIPTION OF THE DRAWINGS

The attached drawings and associated written description disclose an exemplary embodiment of the present invention.

DETAILED DESCRIPTION OF PREFERRED EMBODIMENTS

Figure 1:
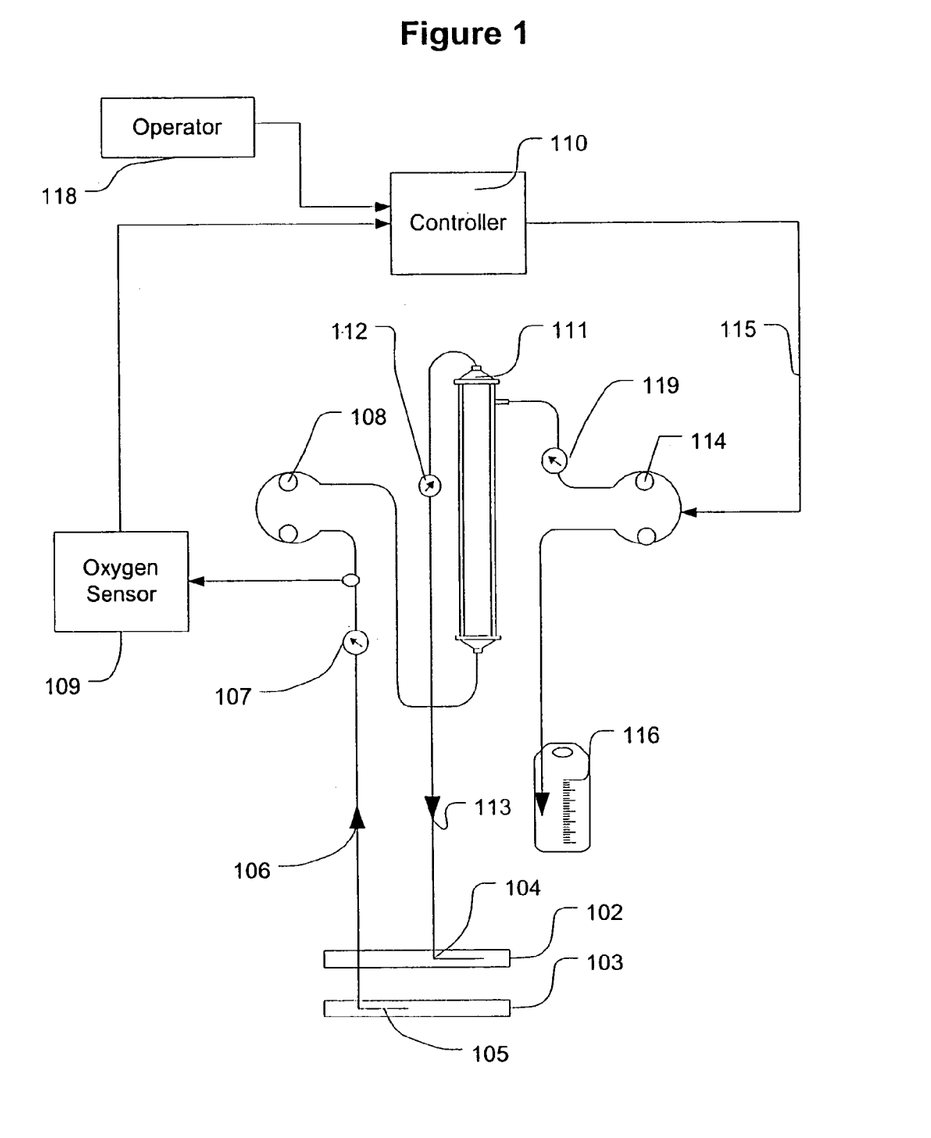
FIG. 1 shows a high level schematic diagram of an ultrafiltration system that detects oxygen level in the blood.

FIG. 1 shows a high level schematic diagram of an ultrafiltration system, such as is disclosed in commonly-owned U.S. Pat. No. 6,887,214 (U.S. patent application Ser. No. 09/660,195 filed Sep. 12, 2000), entitled "Blood Pump Having A Disposable Blood Passage Cartridge With Integrated Pressure Sensor", and U.S. Pat. No. 6,585,675 (U.S. patent application Ser. No. 09/703,702 filed Sep. 12, 2000), entitled "Method And Apparatus For Blood Withdrawal And Infusion Using A Pressure Controller" and filed Nov. 2, 2000, both of which applications are incorporated by reference in their entirety.

Blood is withdrawn from the vein 103 of a human or other mammalian patient using a withdrawal needle 105. The blood flows from the needle into a withdrawal bloodline 106 that is equipped with an in-line pressure sensor 107. The sensor transmits a signal indicative of the blood pressure in the withdrawal line to a computer controller 110. The withdrawal line loops through a blood pump 108. The pump creates a suction (negative) pressure in the withdrawal line that draws blood from the vein and into the line.

The pump also forces blood through a filter 111 that removes excess fluid from the blood. The filter includes a blood passage coupled between a blood inlet and outlet to the filter, a filtering membrane forming a portion of the walls of the passage, and a filtered fluid outlet section on a opposite side of the membrane from the blood passage. The membrane is pervious to fluids, but not to blood cells and relatively large solutes in the blood.

Some percentage of fluid (usually 10 to 20%) in the blood flowing through the blood passage in the filter may pass through the membrane to the outlet section and thereby be filtered from the blood. However, the blood cells and larger proteins in the blood do not pass through the filter membrane and remain in the blood as it exits the filter. The filter has a blood outlet connected to a return line 113 through which flows blood to be infused back into a vein 102 of the patient. The filter has a second output through which flows separated ultrafiltrate (plasma water) that passes in a filtrate line that loops through a metering pump 114 and into a collection bag 116.

The ultrafiltrate pump 114 is capable of generating a negative pressure in the filtrate line (and at the output side of the filter membrane) to assist the flux of ultrafiltrate across the membrane, which has a substantial hydraulic resistance. The pressure level in the filtrate line and in the filtrate output section of the filter is determined by the rotational speed of the ultrafiltrate pump 114. The rotational speed of pumps 108 and 114 is determined by a controller 110 that can be a microcomputer. The controller receives pressure measurements from blood line return sensor 112 and the ultrafiltrate pump sensor 119. The controller is programmed to adjust the ultrafiltrate pump speed to provide a pressure level in the filtrate line to achieve a desired filtration rate. An oxygen sensor 109 is incorporated in the blood tubing 106 prior to the blood pump 108. Signal from the sensor 109 is communicated to the controller 110.

Generally, just prior to the ultrafiltration treatment, an operator, such as a nurse or medical technician, selects certain control settings on the controller for the treatment. The settings (which may be selected by the operator or preprogrammed into the controller, or a combination of both) may include (among other settings) a desired fluid removal rate from the blood. This rate may be applied by the controller to determine the rotational speed of the ultrafiltration pump 114.

The rotational speed of the pump 114 controls the pressure (measured by ultrafiltrate sensor 109) in the output section of the filter. The fluid pressure in the output section is present on one side of the filter membrane. The fluid pressure of the blood in the blood passage is present on the other side of the membrane. The filtration rate is dependent on the pressure difference across the membrane of the filter. The filtration rate is controlled by the pressure in the filtrate outlet section of the filter, assuming that the blood pressure in the filter blood pressure remains constant. Accordingly, the filtration rate is controlled by the speed of the ultrafiltration pump 114 which determines the fluid pressure in the filter outlet section.

A safety feature of the controller is that it adjusts the filtration rate to avoid hypotension of the patient. If too much fluid is removed too rapidly from the blood of the patient, the patient may suffer from hypotension. To avoid hypotension, the controller monitors a feedback signal from the sensor 109 that detects oxygen saturation in the blood. The signal from the sensor 109 is continuously evaluated to determine whether the patient is at risk of suffering hypotension and, if so, reducing the ultrafiltration rate or temporarily interrupting ultrafiltration.

The controller 110 controls the rate of fluid removal from the blood by modifying the rotational speed of the ultrafiltrate pump 114. Control can be exercised by slowly adjusting the rotational speed of the pump 114 with a closed loop controller or by stopping it altogether until the venous volume is refilled. Alternatively, the controller may cyclically stop and start the ultrafiltration pump in a sequence of duty cycles. During a duty cycle, the pump is ON during a portion of each cycle and is OFF during the remainder of the cycle. The portion of the duty cycle during which pump 114 is ON versus OFF determines the filtration rate. Other methods for controlling fluid removal include periodically clamping the ultrafiltrate line to block the output of the filter and prevent fluids from being removed from blood in the filter.

Figure 2:
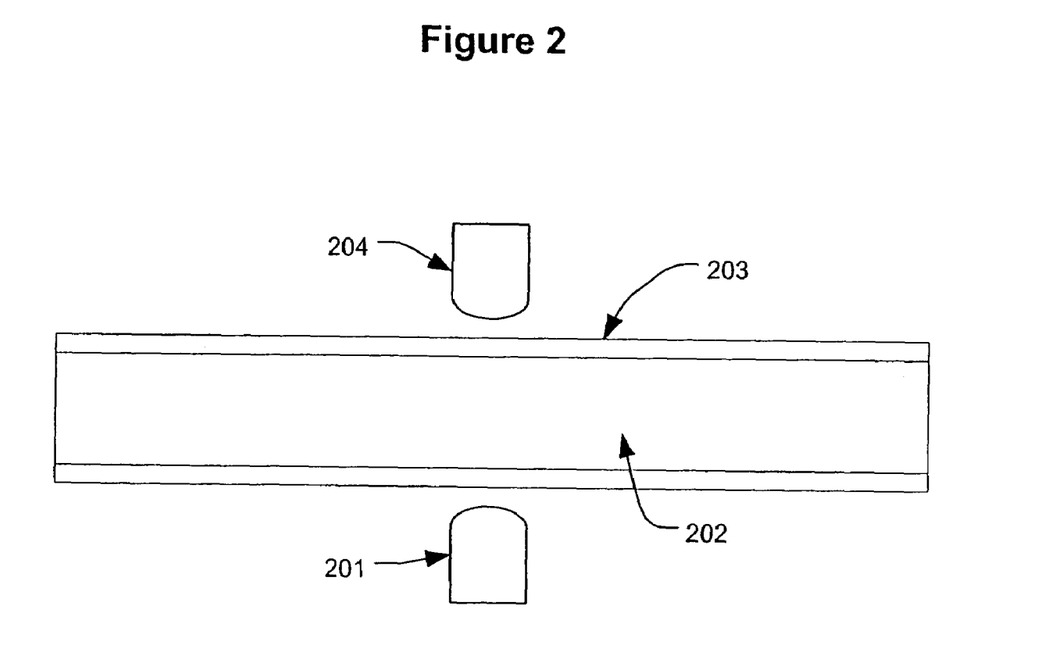
FIG. 2 illustrates a non-invasive sensor system for measuring venous oxygen saturation in a blood filled tube by optical oximetry.

The saturation of oxygen in the blood can be measured by a non-invasive means of oximetry since, during the ultrafiltration, venous blood is passed through the extracorporeal circuit. FIG. 2 shows the venous blood 202 passing through the plastic tube 203 with a transparent wall. The biosensor consists of a photo emitter 204 and a photo receiver 201. The emitter may be a light diode emitting light at a particular wavelength. The photo receiver is coupled with a digital signal processing (DSP) unit in the controller capable of extracting the information about oxygen saturation by the means well known in the field of pulse oximetry. Products for photometric pulse oximetry are available from several manufactures and are well suited for detecting oxygen concentration in a bloodline.

Figure 3:
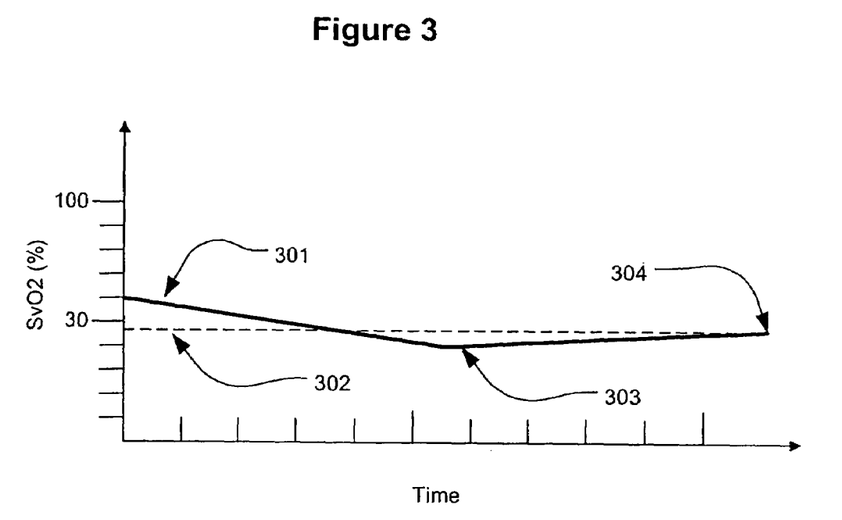
FIG. 3 shows a curve of venous oxygen saturation measurements over time during a course of fluid extraction therapy in a fluid overloaded patient undergoing fluid removal.

FIG. 3 is a chart showing venous oxygen saturation as a function of time for a fluid overloaded patient undergoing fluid removal treatment. If the fluid removal rate exceeds the refilling rate, the cardiac output will be reduced. Since oxygen extraction stays the same, the $SvO_2$ line 301 declines gradually from 60% saturation. When the line crosses the allowed threshold 302, ultrafiltration is stopped by the controller which is monitoring $SvO_2$ level based on the optical blood oxygen sensor. With the ultrafiltration being stopped, the vascular volume is gradually refilled, and consequently, the heart filling pressure is increased, as is cardiac output. At point 303, the process is reversed and the $SvO_2$ starts to increase. Since point 304 is above the preset threshold, ultrafiltration is safely and automatically restarted by the controller.

Figure 4:
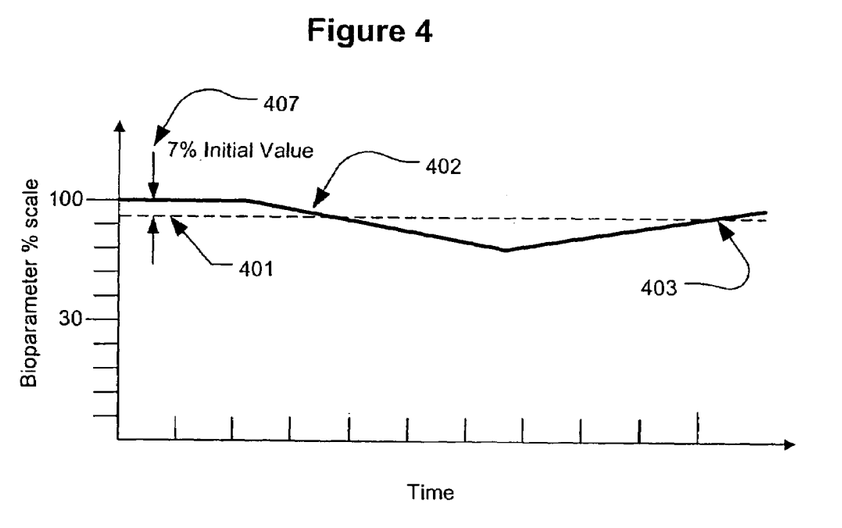
FIG. 4 shows a curve of venous oxygen saturation expressed as a percentage of the baseline value.

FIG. 4 illustrates controlling ultrafiltration using the relative change of a physiologic parameter such as $SvO_2$. At the beginning of treatment 401, a baseline value is established for the physiologic parameter to be monitored. The baseline value is expressed as 100% in the chart shown in FIG. 4. The operator determines what percentage deviation from the baseline is allowed. In this example, a range 407 is set to 7% of baseline. The treatment is started. If in the course of treatment 402 parameter falls below 93% of the baseline ultrafiltration is stopped (or the ultrafiltration rate is slowed) until the condition is restored 403. Once safe condition is restored, treatment continues.

Figure 5:
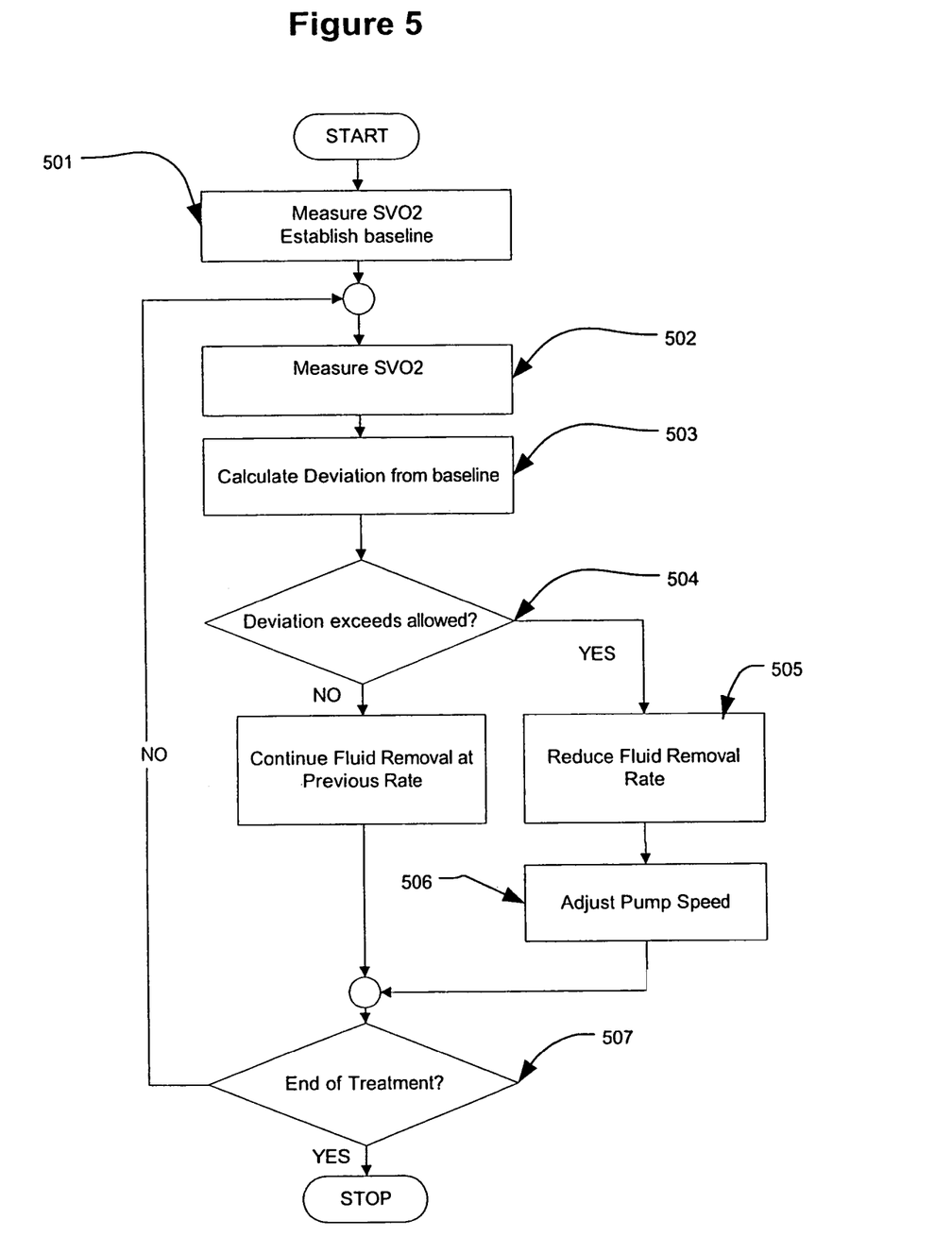
FIG. 5 illustrates a method of controlling ultrafiltration by establishing a predetermined deviation from baseline value of oxygen saturation.
Figure 6:
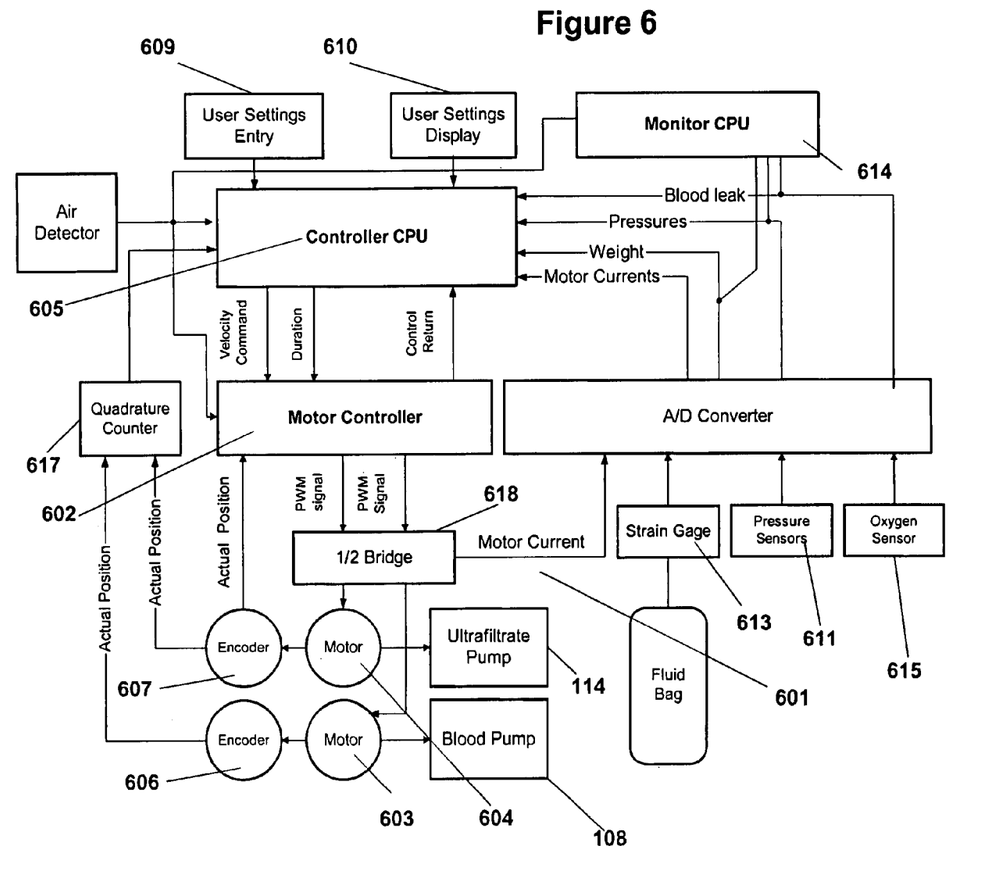
FIG. 6 illustrates design of the controller for ultrafiltration apparatus.

FIG. 5 illustrates an algorithm used by the ultrafiltration controller with an oxygen saturation feedback. The calculations for controlling the flow through the pump 114 are made in the computer-controller 110. The controller receives input from the operator 118 such as a flow rate setting. The operator may enter the desired initial rate of fluid removal or the allowed tolerances to the change of the oxygen saturation of venous blood measured by sensor 109. At the beginning of treatment, a baseline value 501 of $SvO_2$ is established and stored in the computer memory. Periodically the controller measures the reading 502 of the sensor 109. Next, a deviation 503 of the reading from the stored baseline is calculated and compared 504 to the allowed limit. If the deviation exceeds the allowed amount, the fluid removal rate 505 is recalculated and the rotational speed 506 of the ultrafiltrate pump 114 is reduced by the predetermined amount (controller gain). Unless the end of treatment time 507 is reached, the process is repeated starting from an updated measurement 502 of oxygen in blood. More sophisticated algorithms can be employed if the slow continuous control of fluid removal is desired. Well known algorithms such as PI and PID regulators can be employed using deviation of the $SvO_2$ measurement from baseline as input and the speed of ultrafiltrate pump as the output.

FIG. 7 illustrates the electrical architecture of the ultrafiltration controller system 600 (110 in FIG. 1), showing the various signal inputs and actuator outputs to the controller. The user-operator inputs the desired ultrafiltrate extraction rate into the controller by pressing buttons on a membrane interface keypad 609 on the controller. Other user settings may include the maximum flow rate of blood through the system, maximum time for running the circuit to filter the blood, the maximum ultrafiltrate rate the maximum allowed deviation of the venous blood oxygen saturation from the baseline. The settings input by the user are stored in a memory and read and displayed by the controller CPU 605 (central processing unit, e.g., microprocessor or microcontroller) on the display 610.

The controller CPU regulates the pump speeds by commanding a motor controller 602 to set the rotational speed of the blood pump 108 to a certain speed specified by the controller CPU. Similarly, the motor controller adjusts the speed of the ultrafiltrate pump 114 in response to commands from the controller CPU and to provide a particular filtrate flow velocity specified by the controller CPU.

Feedback signals from the pressure transducer sensors 611 are converted from analog voltage levels to digital signals in an A/D converter 616. The digital pressure signals are provided to the controller CPU as feedback signals and compared to the intended pressure levels determined by the CPU. In addition, the digital pressure signals may be displayed by the monitor CPU 614.

The motor controller 602 controls the velocity, rotational speed of the blood and filtrate pump motors 603, 604. Encoders 607 and 606 mounted to the rotational shaft of each of the motors as feedback provide quadrature signals (e.g., a pair of identical cyclical digital signals, but 60° out-of-phase with one another). These signal pairs are fed to a quadrature counter within the motor controller 602 to give both direction and position. The direction is determined by the signal lead of the quadrature signals. The position of the motor is determined by the accumulation of pulse edges. Actual motor velocity is computed by the motor controller as the rate of change of position. The controller calculates a position trajectory that dictates where the motor must be at a given time and the difference between the actual position and the desired position is used as feedback for the motor controller. The motor controller then modulates the percentage of the on time of the PWM signal sent to the one-half 618 bridge circuit to minimize the error. A separate quadrature counter 617 is independently read by the Controller CPU to ensure that the Motor Controller is correctly controlling the velocity of the motor. This is achieved by differentiating the change in position of the motor over time.

The monitoring CPU 614 provides a safety check that independently monitors each of the critical signals, including signals indicative of blood leaks, pressures in blood circuit, weight of filtrate bag, motor currents, air in blood line detector and motor speed/position. The monitoring CPU has stored in its memory safety and alarm levels for various operating conditions of the ultrafiltrate system. By comparing these allowable preset levels to the real-time operating signals, the monitoring CPU can determine whether a safety alarm should be issued, and has the ability to independently stop both motors and reset the motor controller and controller CPU if necessary.

Input from the Oxygen sensor 615 is converted to a digital signal similar to other analog signals. Alternatively, if a microprocessor based sensor is used, it can be already in a digital for. This signal input allows CPU 605 to recalculated the desired ultrafiltration rate and control the rotational speed of the pump 114 to prevent reduction in the patient's cardiac output and hypotension without help from the operator.

The preferred embodiment of the invention now known to the invention has been fully described here in sufficient detail such that one of ordinary skill in the art is able to make and use the invention using no more than routine experimentation. The embodiments disclosed herein are not all of the possible embodiments of the invention. Other embodiments of the invention that are within the sprite and scope of the claims are also covered by this patent.

What claimed is:

1. A system for treating blood from a patient comprising:
    an extracorporeal circuit having a blood passage including a blood withdrawal tube, a filter and an infusion tube, said filter having filter blood passage in fluid communication with the withdrawal tube, a blood outlet in fluid communication with the infusion tube, a filter membrane in fluid communication with the blood passage, a filter output section on a side of the membrane opposite to the blood passage, and a filtrate output line in fluid communication with the filter output section;
    a biosensor coupled to said extracorporeal circuit and generating a feedback signal indicative of cardiac output of the patient;
    a filtrate pump coupled to the filtrate output line and adapted to draw filtrate fluid from the filter at a controlled filtration rate, and
    a filtrate pump controller regulating the controlled filtration rate based on the feedback signal, wherein the pump controller includes a processor and a memory storing a control algorithm to determine whether a feedback signal threshold is beyond the feedback signal and storing a baseline feedback signal generated by the biosensor during an initial phase of blood filtration treatment, said controller programmed to execute the control algorithm to reduce the controlled filtration if the feedback signal exceeds the feedback signal threshold, wherein the signal threshold is automatically determined by the controller and is a function of the baseline feedback signal.

2. A system as in claim 1 wherein the feedback signal is indicative of an oxygen level in the venous blood.

3. A system as in claim 1 wherein the feedback signal threshold is determined based on a sum of a feedback signal obtained during an initial phase of a treatment of the patient and a predetermined current feedback signal change.

4. A system as in claim 1 wherein the filter is a hemofilter.

5. A system as in claim 1 wherein the treatment device is a dialysis filter.

6. A system as in claim 1 wherein the treatment device is an ultrafiltration filter.

7. A system as in claim 1 wherein said control algorithm includes a control step of automatically increasing the reduced filtrate flow, if the feedback signal is within the threshold.

* * * * *